(12) United States Patent
Lubatschowski et al.

(10) Patent No.: US 10,799,392 B2
(45) Date of Patent: Oct. 13, 2020

(54) CONTROLLER FOR A SURGICAL LASER

(75) Inventors: Holger Lubatschowski, Hannover (DE); Omid Kermani, Cologne (DE); Georg Gerten, Bonn (DE); Uwe Oberheide, Cologne (DE)

(73) Assignee: ROWIAK GMBH, Hannover (DE)

( * ) Notice: Subject to any disclaimer, the term of this patent is extended or adjusted under 35 U.S.C. 154(b) by 1938 days.

(21) Appl. No.: 13/336,863

(22) Filed: Dec. 23, 2011

(65) Prior Publication Data

US 2012/0172852 A1   Jul. 5, 2012

(30) Foreign Application Priority Data

Dec. 23, 2010 (EP) ..................................... 10196925

(51) Int. Cl.
*A61F 9/008* (2006.01)

(52) U.S. Cl.
CPC .......... *A61F 9/008* (2013.01); *A61F 9/00838* (2013.01); *A61F 2009/0087* (2013.01); *A61F 2009/00895* (2013.01); *A61F 2009/00897* (2013.01)

(58) Field of Classification Search
CPC .................. A61F 9/008; A61F 9/00838; A61F 2009/00897; A61F 2009/00895; A61F 2009/0087
USPC .............................................. 606/4–6, 10–13
See application file for complete search history.

(56) References Cited

U.S. PATENT DOCUMENTS

| 7,655,002 | B2* | 2/2010 | Myers ..................... | A61F 9/008 606/10 |
|---|---|---|---|---|
| 8,262,646 | B2* | 9/2012 | Frey ........................ | A61F 9/008 606/10 |
| 9,180,051 | B2* | 11/2015 | Frey ........................ | A61F 9/008 |
| 2004/0199149 | A1 | 10/2004 | Myers et al. | |
| 2005/0165387 | A1 | 7/2005 | Lubatschowski et al. | |
| 2010/0004641 | A1 | 1/2010 | Frey et al. | |
| 2010/0130967 | A1 | 5/2010 | Glasmacher et al. | |

(Continued)

FOREIGN PATENT DOCUMENTS

WO   2010/075571 A2   7/2010

OTHER PUBLICATIONS

European Search Report dated Jun. 21, 2011 for EP Patent Application No. 10196925.1, 7 pages.

(Continued)

*Primary Examiner* — Ahmed M Farah
(74) *Attorney, Agent, or Firm* — Kilpatrick Townsend & Stockton

(57) ABSTRACT

The invention relates to a controller for a surgical laser. According to the invention, the controller is adapted to control a laser in order to produce two or more three-dimensional compression zones, each comprising a plurality of lesions, inside a lens cortex of a crystalline lens of the eye using a laser pulse or multiple laser pulses, wherein the controller is adapted such that a laser can be calibrated with respect to a reference point within the lens, and each of the compression zones produced has a length in a radial direction, a depth in a direction parallel to the optical or visual axis and an average width in a direction parallel to a tangent of the lens cortex, wherein the sum of the average widths of all compression zones is 0.1 to 2 millimeter for every 1 diopter of desired gain in accommodation amplitude of the lens.

15 Claims, 12 Drawing Sheets

(56) References Cited

U.S. PATENT DOCUMENTS

Figure 1:
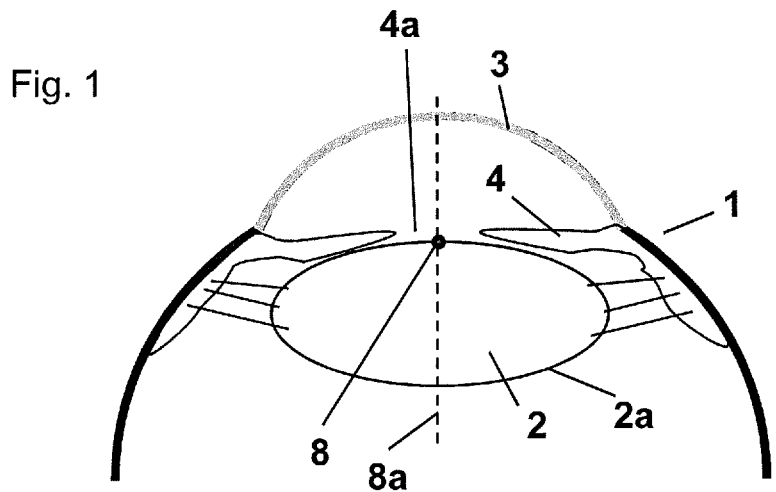

2011/0196350 A1* 8/2011 Friedman ................ A61F 9/008
  606/6
2013/0103013 A1* 4/2013 Esposito ............. A61F 9/00812
  606/5

OTHER PUBLICATIONS

European Examination Report dated May 6, 2013 for EP Patent Application No. 10196925.1, 4 pages.

\* cited by examiner

CONTROLLER FOR A SURGICAL LASER

CROSS-REFERENCE TO RELATED APPLICATION

This application claims the benefit of priority to European Application No. EP 10 196 925.1, filed Dec. 23, 2010, the disclosure of which is herein incorporated by reference.

The invention relates to a controller for a surgical laser, which is adapted to control a laser that can be connected to the controller. The invention further relates to a surgical laser and a method for the treatment of a crystalline lens of the eye with a lens nucleus and a lens cortex.

Starting at the age of about 45 years, there begins a continuous decrease of the ability of the crystalline lens of the human eye to accommodate. This is manifested by the occurrence of farsightedness due to age (Presbyopia). Due to its decreasing elasticity, the crystalline lens is no longer able to thicken sufficiently and to decrease its radius of curvature as necessary for sharp imaging of near objects on the retina. Unaffected by the decreasing elasticity, the ciliary muscle as well as the capsular bag surrounding the lens of the eye, both usually remain active and elastic.

WO 2009/007990 A2 describes a method for ablating a presbyopic lens for restoring accommodation in a human eye by reducing the volume of the lens. U.S. Pat. No. 7,655,002 B2 discloses the treating of a crystalline lens through the creation of microspheres within the lens in selected locations. US 2005/0165387 A1 proposes a controller for a surgical laser, adapted to control a laser that can be connected to the controller to produce a plurality of cut surfaces inside a crystalline lens using multiple laser pulses, and particularly to simultaneously produce a multiplicity of cut surfaces in a preselected arrangement with respect to one another.

The task of the present invention is to provide an improved controller for a surgical laser, which is adapted to control a laser that can be connected to the controller. It is a further task of the invention to provide an improved surgical laser system and an improved method for the treatment of a crystalline lens of the eye with a lens nucleus and a lens cortex.

According to the invention, a controller for a surgical laser is provided. A laser is to be understood as a laser system and preferably comprises a laser source, a beam delivery, a patient interface, and an imaging system. The controller preferably controls the interaction between the beam delivery system, the patient interface and the imaging system.

According to the invention, the controller is adapted to control a laser that can be connected to the controller in order to produce two or more three-dimensional compression zones, each comprising a plurality of lesions, inside a lens cortex or a lens nucleus of a crystalline lens of the eye using a laser pulse or multiple laser pulses, wherein the controller is adapted such that a laser can be calibrated with respect to a reference point within the crystalline lens, and each of the compression zones produced has a length in a radial direction in relation to the crystalline lens in a plane perpendicular to the optical or visual axis corresponding to an extension of the lens cortex in a radial direction in a plane perpendicular to the optical or visual axis, each of the compression zones produced has a depth in a direction parallel to the optical or visual axis corresponding to an extension of the lens cortex in a direction parallel to the optical or visual axis, and each of the compression zones produced has an average width in a direction parallel to a tangent of the lens cortex and in a plane perpendicular to the optical or visual axis of the eye, wherein the sum of the average widths of all compression zones is 0.1 to 2 millimeter for every 1 diopter of desired gain in accommodation amplitude of the crystalline lens.

Compressions zones, comprising a plurality of lesions inside the crystalline lens, change the lines of traction inside the crystalline lens in comparison to their arrangement in the untreated state of the crystalline lens, thereby increasing the elasticity of the crystalline lens.

WO 2009/007990 A2 describes a method for ablating a presbyopic lens for restoring accommodation in a human eye. Here, a laser beam carries out multiple photoablations in circular way within the lens and behind the iris and preferably near the edge or equator to re-establish accommodation of the lens. However, in this invention the laser has to reduce the volume of the lens by photo fragmentation and vaporisation of the lens material. The idea behind is, that the inventors assume, that presbyopia is caused by the continuous growing of the lens during lifetime. Once the diameter of the lens on the equator is too big to keep the zonular fibers under tension, the ciliary body is not able anymore to mold the lens in order to change the power of refraction. The present invention is based on the finding, that in order to re-establish accommodation of the lens, it is not necessary to reduce the volume of the lens by photo fragmentation and vaporisation of the lens material preferably near the edge or equator of the lens like in WO 2009/007990 A2. In the present invention, no change of volume of the lens is intended.

The present invention is based on the following physical model: a deformable substance (like the lens material), which is surrounded by an elastic membrane (like the lens capsule) tends to become a sphere due to the surface tension which is applied by the elastic membrane. If the lens material is too stiff (like in a presbyopic lens) the surface tension of the elastic membrane is too weak to mold the lens in a spherical shape. One way to reduce the stiffness of the lens material is to induce compression zones inside the lens material.

The invention is based on the finding that a certain desired change in refractive power and thus a gain in accommodation amplitude of the crystalline lens can be obtained by creating compression zones with a specific volume within the lens cortex. The inventive characteristics of this volume of the compression zones is that each of the compressions zones extends basically along the length and depth of the lens cortex, i.e. the extension of the lens cortex in a radial direction in a plane perpendicular to the optical or visual axis and in a direction parallel to the optical or visual axis. All compression zones together have a total average width of is 0.1 to 2 millimeter for every 1 diopter of desired gain of accommodation amplitude of the crystalline lens. This relation between the volume of the compression zones and the desired change in refractive power or gain in accommodation amplitude, respectively, leads to a more precise possibility to correct vision deficiencies.

In an embodiment of the invention, the width of each of the compressions zones varies along the length of the respective compressions zones and the average width is the average value of the varying width.

In a cross section perpendicular to the optical or visual axis, the width of the individual compression zones may differ, i.e. the width of the compression zone closer to the inner circumference of the lens cortex may differ from a width of the compression zone closer to the outer circumference of the lens cortex.

The invention can be improved in that the controller is adapted to direct a laser such that each of the compression zones has the form of a cuboid or a segment of a cylinder.

Compression zones with an approximately constant length, depth and width, i.e. a length, depth and width that vary only to a very small extent, approximately form cuboids. Alternatively, compression zones may have the form of a segment of a cylinder, i.e. the cross section of compression zones in a plane perpendicular to the optical or visual axis have the form of segments of a circle or a pie slices.

In an embodiment of the invention, the depth of each of the compressions zones varies along the length of the respective compressions zones. For example, a compression zone may have a larger depth close to the lens nucleus and a smaller depth in a region with a higher radial distance to the lens nucleus.

The invention can be improved in that the controller is adapted to direct a laser such that the sum of the average widths of all compression zones is 0.1 to 2 millimeter, preferably 0.7 to 1.5 millimeter, for every 1 diopter of gain in accommodation amplitude of the crystalline lens. The invention can be improved in that the controller is adapted to direct a laser such that the sum of the average widths of all compression zones is 0.75 to 1.2 millimeter, preferably approximately 0.9 millimeter, for every 1 diopter of gain in accommodation amplitude of the crystalline lens. The invention can be improved in that the controller is adapted to direct a laser such that the average width g in micrometer of each compression zone corresponds to $$g = 10 \frac{2 \prod r}{n} \left(1 - \sqrt{\frac{L}{L + (d*80)}}\right);$$

wherein r is the radius of a nucleus of the crystalline lens in micrometer, n is the number of compression zones, L is the length of the nucleus of the crystalline lens in a direction parallel to the optical or visual axis in micrometer and d is the desired gain in accommodation amplitude in diopter.

These preferred embodiments are based on the finding that the particular volumes of the compression zones lead to a desired gain in accommodation amplitude in a determinable manner.

The invention can be improved in that the controller is adapted to direct a laser such that the compression zones are arranged equidistant to each other in a direction circumferential of the lens cortex or the lens nucleus. This embodiment is particularly preferred since it leads to a more uniform accommodation of the lens.

The invention can be improved in that the controller is adapted to direct a laser such that four compression zones are arranged in the form of a cross in a plane perpendicular to the optical or visual axis. The invention can be improved in that the controller is adapted to direct a laser such that a plurality of compression zones is produced that forms a star-like pattern in a plane perpendicular to the optical or visual axis. These preferred embodiments provide for a particularly advantageous accommodation of the lens.

The invention can be improved in that the controller is adapted to direct a laser to produce the lesions such that they act as sliding planes.

The sliding planes reduce the internal friction of the lens material and make it more flexible. The sliding planes can be generated by laser pulses. The sliding planes itself are very thin. Ideally, they have infinitesimal thickness without any volume. In practice, minimal changes in volume may occur, but are negligible in comparison to the reduction in volume intended and realised by the solution of WO 2009/007990 A2.

According to the improved embodiment, the lesions are produced in the crystalline lens by a laser pulse or multiple laser pulses. Usually, the laser pulses produce lesions or faults of less than 10 µm in diameter, preferably of 1-5 µm in diameter, in which the fibrils of the crystalline lens are destroyed. The cavities created at the faults are filled with fluid of the crystalline lens. The laser pulses are produced by a laser emitting device. The term "laser" is meant to comprise the laser emitting device.

The invention can be improved in that the controller is adapted to direct a laser such that the compression zones are located within an annular region delimited by an inner and an outer diameter in a first plane of the crystalline lens with respect to the reference point.

According to the improved embodiment, an annular region is defined within the crystalline lens and the compression zones are located within this annular region. The annular region is defined by an inner and an outer diameter or an inner and an outer radius with respect to a center of the annular region. This annular region with its inner and outer diameter is located within a first plane in the crystalline lens. Preferably, this first plane is approximately parallel to a plane comprising an opening of an iris covering the crystalline lens, the pupil, and approximately perpendicular to the optical axis of the eye or the visual axis respectively. Preferably, the annular region has the shape of, e.g., a torus, a section of a hollow cylinder, a section of a hollow conus, or the like.

According to the improved embodiment, the annular region of the crystalline lens is located within the crystalline lens such that the pupil (opening of the iris) covering the crystalline lens is smaller than the annular region. This is meant to be the case for the iris being in a non-dilated state. With a non-dilated state it is meant that the pupil has a diameter varying in a range of dimensions occurring during normal vision of a patient, e.g. due to changes in light intensity or changes in distance of objects in focus. In the sense of the current invention, non-dilated means a state of the iris without any artificial dilating stimuli like dilating drugs. The natural variation of the diameter of the pupil due to changing lighting conditions is much smaller than the dilatation of the pupil resulting from artificial stimuli like dilating drugs. Thus, the annulus within the crystalline lens comprising the compression zones is covered by the iris during normal vision of the patient.

The improved embodiment has the advantage, that a center area of the crystalline lens along the optical axis of the eye or the visual axis respectively, which is not covered by the iris during normal vision, is not affected by the treatment, i.e. the compressions zones are not located in this area. Thus, adverse effects on the line of sight and the vision quality, particularly the long-term vision quality, due to compressions zones in that area of the crystalline lens not covered by the iris in a non-dilated state are avoided or at least reduced.

In a further preferred embodiment of the invention the controller is adapted to define a starting point and an end point of each compression zone relative to the reference point prior to producing the compression zones. The reference points can be determined by imaging methods such as Optical Coherence Tomography (OCT), Scheimpflug Imaging or ultra sound imaging. One preferred reference point could be the apex of the crystalline lens.

In this way, each of the compression zones can be produced in an exact desired position within the crystalline lens in order to place the lesions in positions that are preferred in order to change the characteristics of the crystalline lens with respect to its flexibility.

In a preferred embodiment of the invention the controller is adapted to define the starting point and the end point of each compression zone such that the compression zones are located within the crystalline lens and spaced apart from a capsule of the crystalline lens.

In this embodiment it is ensured that the compression zones do not penetrate the capsule of the crystalline lens. Thus, the capsule of the crystalline lens as well as a volume adjacent the capsule, preferably a volume extending 100-500 micrometer from the capsule in direction of the center of the crystalline lens, remain intact and without lesions.

In a preferred embodiment of the invention the controller is adapted to define the starting point and the end point of each compression zone such that the compression zones do not overlap. It is further preferred that the controller is adapted to define the starting point and the end point of each lesion such that the lesions do not overlap.

In this way, it is ensured that multiple compressions zones and/or lesions spaced apart from each other are produced rather than compressions zones and/or lesions that overlap and thus form one continuous compressions zone and/or lesion. With the present preferred embodiment it is ensured that the multiple compressions zones and/or lesions only change the characteristics of the lens with respect to flexibility but do not lead to a significant change in volume of the lens.

In a further preferred embodiment, the controller is adapted to locate a center of the annular region of the crystalline lens on the optical axis of the eye or the visual axis respectively.

This embodiment relates to a co-axial arrangement of the annular region of the crystalline lens and the pupil with the center of the annular region of the crystalline lens and a center of the opening of the iris both located on a single axis approximately perpendicular to the first plane. This embodiment is preferred, since it makes sure that the annulus forming the annular region is larger than the pupil in a non-dilated state, including the varying diameters of the opening of the iris (pupil) during usual sight of a patient due to changes in light intensity or distance of objects in focus.

In a further embodiment, the controller is adapted to define the annular region of the crystalline lens such that it has an inner diameter of about 2-8 millimeter, preferably about 3-7 millimeter; and the annular region of the crystalline lens has an outer diameter of about 6-10 millimeter, preferably about 7 millimeter. These dimensions are particularly preferred with regard to the typical dimensions of the human eye and the effects usually obtained by dilating drugs.

In a further preferred embodiment, the controller is adapted to define the outer diameter of the annular region of the crystalline lens with a safety clearance to a capsule of the crystalline lens. This safety clearance preferably is about 100-500 micrometer. This embodiment is based on the finding that producing compression zones and/or lesions too close to the capsule of the crystalline lens, i.e. the outer periphery of the crystalline lens, may lead to negative effects such as cataract.

According to further preferred embodiment, the controller is adapted to determine the outer diameter of the annular region depending on values provided to the controller regarding one or more characteristics of a laser, regarding a diameter of an opening of a dilated iris covering the crystalline lens or regarding a distance between the compression zones and an iris covering the crystalline lens in a direction of the optical axis of the eye or the visual axis respectively. Preferably, the characteristics of the device emitting the laser pulses are one or more of the following parameters: a diameter of a focal spot size of the emitted laser pulse, a location of a focal point, an intensity of the emitted laser pulses, a wavelength of the emitted pulses, a pulse duration of the emitted pulses, a repetition rate of the emitted pulses.

As described above, it is important to ensure that the radiation emitted by a laser does not accidently damage tissue of the eye or gets refracted or shielded, leading to possibly incorrect or insufficient lesions. Therefore it is preferred, that the outer diameter of the annular region of the crystalline lens is determined depending on the kind of laser emitting the pulses. Important characteristics used for the defining of the outer diameter of the annular region are e.g. the diameter of the focal spot size of the emitted laser pulse and a location of a focal point—and thus the resulting conus of radiation emitted by the laser—as well as the intensity of the emitted radiation. These characteristics primarily influence the risk of accidental damages or refraction and shielding by the adjacent iris. Preferred laser specifications are the following: numerical aperture of approx. 0.01-0.6, preferably 0.15-0.35, wavelength of 800-1400 nm, pulse length of 1 fs-1000 fs, pulse energy of 1 pJ-1 mJ.

In a preferred embodiment, the controller is adapted to define the outer diameter of the annular region of the crystalline lens depending on a distance between the compression zones and the iris in a direction of the optical axis of the eye or the visual axis respectively.

As described above, a further parameter influencing the risk of accidently damaging other tissue or laser radiation getting refracted or shielded is the location of the compression zones and the lesions within to be produced along a direction of the optical axis of the eye or the visual axis respectively. For example, with a wide radiation conus resulting from a large aperture, the area covered by the radiation gets larger the deeper within the crystalline lens the lesions are to be produced. The distance between the lesions to be produced and the iris in a direction of the optical axis of the eye or the visual axis respectively therefore is a relevant parameter for determining a maximum outer diameter of the annular region for minimizing the risk of accidental tissue damages or incorrect or insufficient lesions.

According to a second aspect to the invention a surgical laser system is provided, wherein a laser is connected to a controller according to any one of the embodiments described above. The laser system preferably comprises a laser source, a beam delivery, a patient interface, and an imaging system. A controller for a surgical laser preferably controls the interaction between the beam delivery system, the patient interface and the imaging system.

According to a third aspect of the invention a method for the treatment of a crystalline lens of the eye with a lens nucleus and a lens cortex is provided, wherein two or more three-dimensional compression zones, each comprising a plurality of lesions, are produced inside the lens cortex using a laser pulse or multiple laser pulses; wherein at least one reference point of the crystalline lens is identified and each of the compression zones has a length in a radial direction in relation to a center of the lens and in a plane perpendicular to the optical or visual axis corresponding to an extension of the lens cortex in a radial direction in a plane perpendicular to the optical or visual axis and each of the compression zones has a depth of each compression zone in a direction parallel to the optical or visual axis corresponding to an extension of the lens cortex in a direction parallel to the optical or visual axis, and each of the compression zones has an average width in a direction parallel to a tangent of the lens cortex and in a plane perpendicular to the optical or visual axis and the wherein the sum of the average widths of all compression zones is 0.1 to 2 millimeter for every 1 diopter of desired gain in accommodation amplitude of the crystalline lens.

According to an embodiment of the method, the width of each of the compressions zones varies along the length of the respective compressions zones and the average width is the average value of the varying width.

According to a further embodiment of the method, each of the compression zones has the form of a cuboid or a segment of a cylinder.

According to a further embodiment of the method, the sum of the average widths of all compression zones is 0.1 to 2 millimeter, preferably 0.7 to 1.5 millimeter, for every 1 diopter of gain in accommodation amplitude of the crystalline lens.

According to a further embodiment of the method, the sum of the average widths of all compression zones is 0.75 to 1.2 millimeter, preferably approximately 0.9 millimeter, for every 1 diopter of gain in accommodation amplitude of the crystalline lens.

According to a further embodiment of the method, the average width g in micrometer of each compression zone corresponds to $$g = 10 \frac{2\prod r}{n}\left(1 - \sqrt{\frac{L}{L + (d*80)}}\right);$$

wherein r is the radius of the nucleus of the crystalline lens in micrometer, n is the number of compression zones, L is the length of the nucleus of the crystalline lens in a direction parallel to the optical or visual axis in micrometer and d is the gain in accommodation amplitude in diopter.

According to a further embodiment of the method, the compression zones are arranged equidistant to each other in a direction circumferential of the lens cortex or the lens nucleus.

According to a further embodiment of the method, four compression zones are arranged in the form of a cross in a plane perpendicular to the optical or visual axis.

According to a further embodiment of the method, a plurality of compression zones is produced that forms a star-like pattern in a plane perpendicular to the optical or visual axis.

According to a further embodiment of the method, the lesions are produced such that they act as sliding planes.

According to a further embodiment of the method, the compression zones are located inside the crystalline lens within an annular region of the crystalline lens, said annular region being delimited by an inner and an outer diameter in a first plane of the crystalline lens; wherein the annular region of the crystalline lens is arranged such that the inner diameter of the annular region of the crystalline lens is equal to or larger than a diameter of an opening of an iris (pupil) covering the crystalline lens in a non-dilated state of the iris.

According to a further embodiment of the method, a starting point and an end point of each compression zone relative to the reference point is defined prior to producing the compression zones.

According to a further embodiment of the method, the starting point and the end point of each compression zone are defined such that the compression zones are located within the crystalline lens and spaced apart from a capsule of the crystalline lens.

According to a further embodiment of the method, the starting point and the end point of each compression zone are defined such that the compression zones do not overlap.

According to a further embodiment of the method, prior to producing the compression zones the iris is dilated artificially by drugs such that a diameter of the opening of the iris (pupil) is larger than the outer diameter of the annular region of the crystalline lens.

In order to produce the compressions zones in the annular region of the crystalline lens, which is covered by the iris in a non-dilated state, it is preferred to dilate the iris, preferably using respective dilating drugs, prior to producing the compressions zones. This has the advantage, that the annular region of the crystalline lens is not covered by the iris during the producing of the compressions zones. Since the compressions zones with multiple lesions is produced using a laser pulse or multiple laser pulses, in this preferred embodiment the laser pulses can be directed directly to the annular region where the compressions zones is to be produced and do not have to pass through the iris or are refracted by the iris. Refraction of the radiation may lead to inaccurate or insufficient lesions. It is particularly preferred that the iris is dilated such that its opening is larger than the annulus forming the annular region. This embodiment is particularly preferred since it reduces the risk of accidentally damaging the iris or laser pulses getting refracted by the iris also when a lesion is located close to the outer diameter of the annular region. Thus, the safety of the treatment increases and the risk of accidentally damaging healthy tissue is reduced.

According to a further embodiment of the method, prior to producing the compression zones and after dilating the iris a diameter of the opening of the iris (pupil) in the dilated state is measured and the outer diameter of the annular region of the crystalline lens is defined such that it is smaller than the diameter of the opening of the iris in the dilated state.

In this preferred embodiment, the outer diameter of the annular region depends on the diameter of the opening of the iris in its dilated state. The advantage of this embodiment is, that in this way the dimension of the annular region can be adapted to the individual dimensions of the eye of a patient. Particularly, the actual effect of dilating drugs on an individual patient can be taken into account when defining the outer diameter of the annular region. This is particularly preferred, since these effects may vary from patient to patient in a magnitude of several millimeters. With this embodiment it is ensured, that the annular region is located fully within the pupil in the dilated state and a laser pulse producing a plurality of lesions within the annular region does not damage the iris or gets refracted by the iris. Thus, the safety of the treatment can be increased, since it is adapted to individual parameters of individual patients.

According to a further embodiment of the method, prior to dilating the iris a diameter of the opening of the iris (pupil) in the non-dilated state is measured and the inner diameter of the annular region is defined such that it is equal to or larger than the diameter of the opening of the iris (pupil) in the non-dilated state. It is particularly preferred, that the diameter of the opening of the iris in the non-dilated state is measured in a dim environment or in darkness.

With these embodiments it is made sure that the annular region of the crystalline lens is arranged such that the inner diameter of the annular region of the crystalline lens is equal to or larger than a diameter of an opening of an iris covering the crystalline lens in a non-dilated state of the iris by measuring the diameter of the pupil prior to dilating it. This is particularly preferred, since the natural variation of the diameter of the pupil due to changing lighting conditions, e.g. during day and night, varies for individual patients. A further advantage is realized when the diameter of the pupil is not only measured in a non-dilated state during daylight, but also or alternatively in a dim environment or in darkness in order to identify the maximal diameter of an individual's pupil in a non-dilated state, i.e. under natural dilatation due to lighting conditions and not in an dilated state resulting from dilating drugs.

According to a further embodiment of the method, a center of the annular region of the crystalline lens is located on the optical axis of the eye or the visual axis respectively.

According to a further embodiment of the method, the annular region of the crystalline lens has an inner diameter of about 2-8 millimeter, preferably about 3-7 millimeter; and the annular region of the crystalline lens has an outer diameter of about 6-10 millimeter, preferably about 7 millimeter.

According to a further embodiment of the method, the outer diameter of the annular region of the crystalline lens is defined with a safety clearance to a capsule of the crystalline lens.

According to a further embodiment of the method, the safety clearance preferably is about 100-500 micrometer.

According to a further embodiment of the method, prior to producing the compression zones the outer diameter of the annular region of the crystalline lens is defined depending on one or more characteristics of a device emitting the laser pulses; and wherein preferably the characteristics of the device emitting the laser pulses are one or more of the following parameters: a diameter of a focal spot size of the emitted laser pulse, a location of a focal point, an intensity of the emitted laser pulses, a wavelength of the emitted pulses, a pulse duration of the emitted pulses, a repetition rate of the emitted pulses.

According to a further embodiment of the method, prior to producing the compression zones the outer diameter of the annular region of the crystalline lens is defined depending on a distance between the compression zones and the iris in a direction of the optical axis of the eye or the visual axis respectively.

As to the advantages, preferred embodiments and details of these further aspects and preferred embodiments, reference is made to the corresponding aspects and embodiments described with respect to the inventive controller and its preferred embodiments above.

Figure 2:
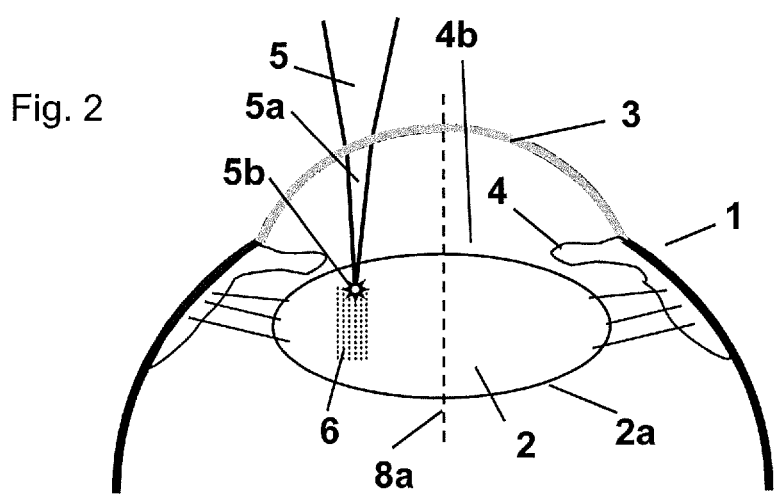
Figure 3:
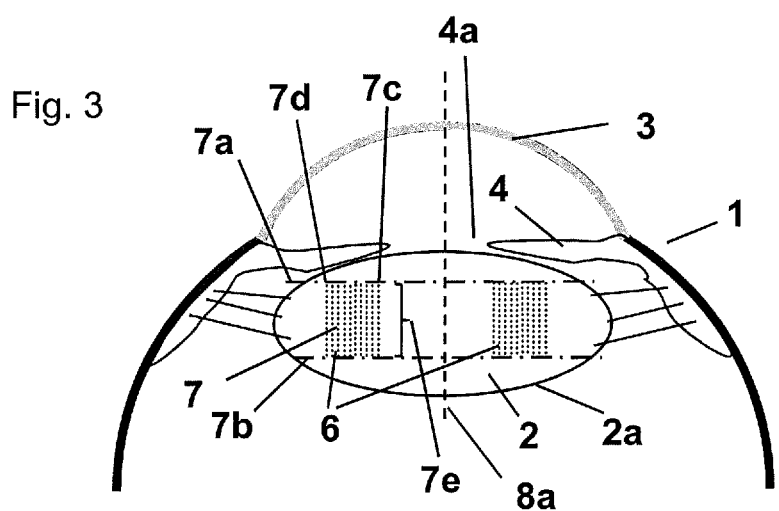
Figure 4A:
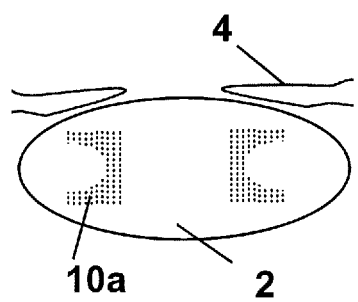
Figure 4B:
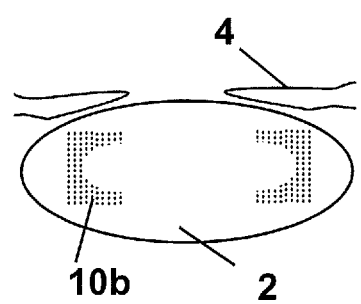
Figure 4C:
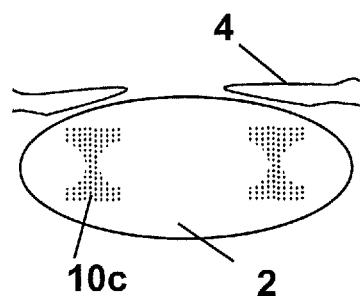
Figure 4D:
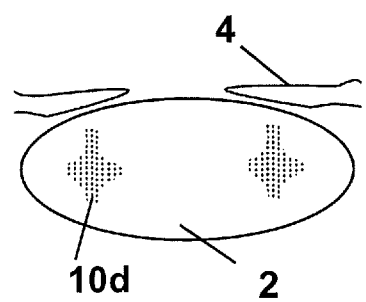
Figure 6:
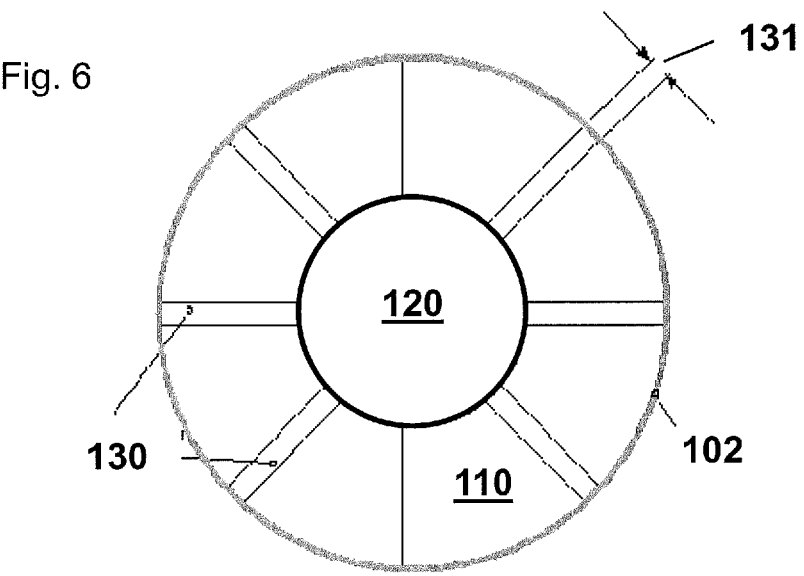
Figure 7:
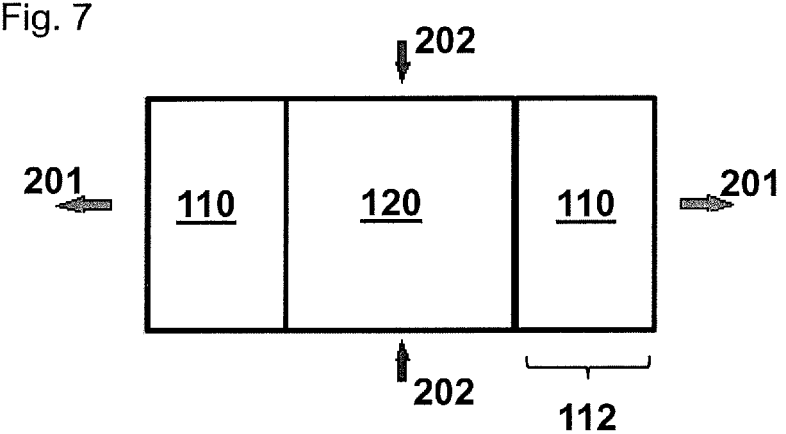
Figure 8:
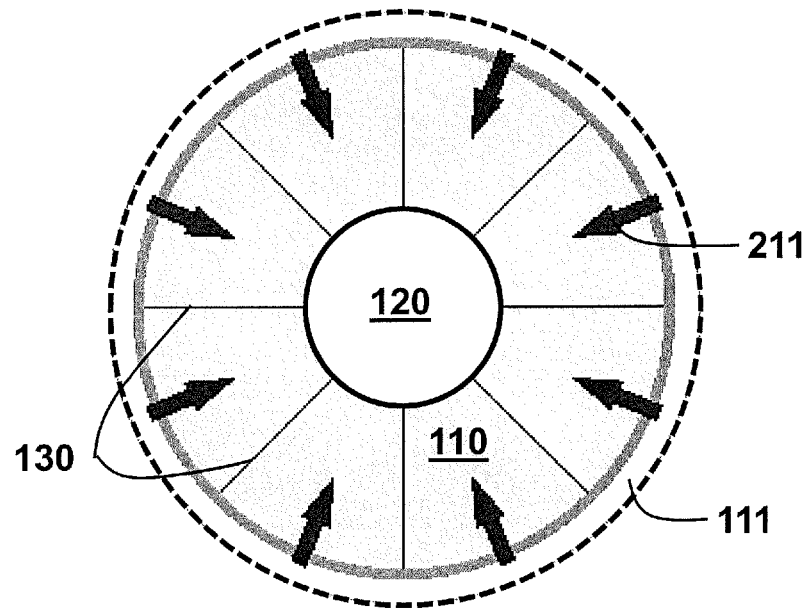
Figure 9:
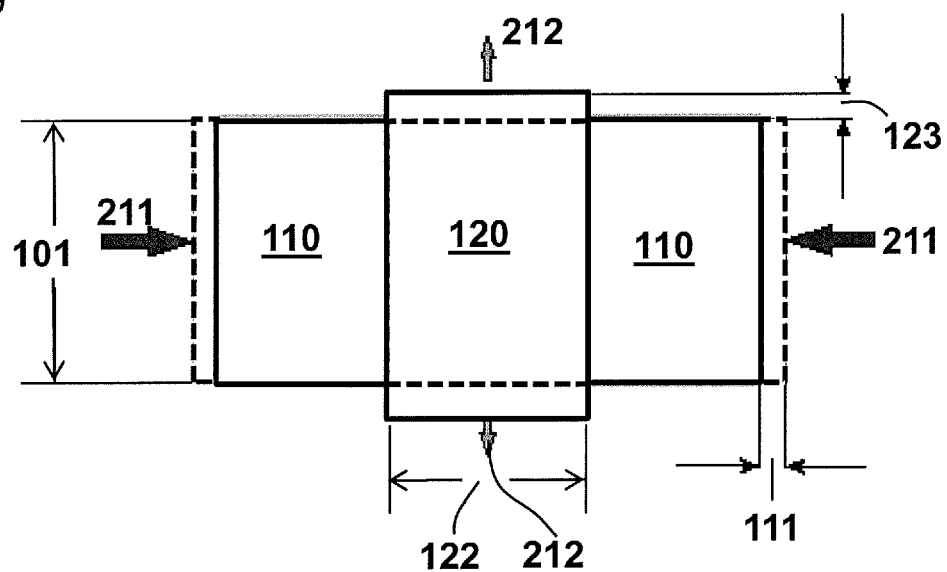
Figure 10:
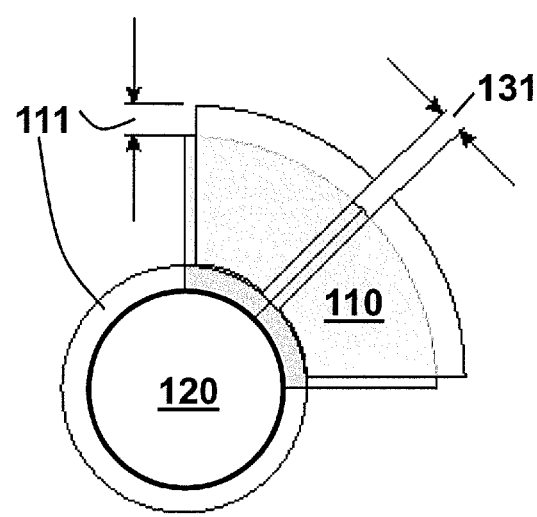
Figure 11A:
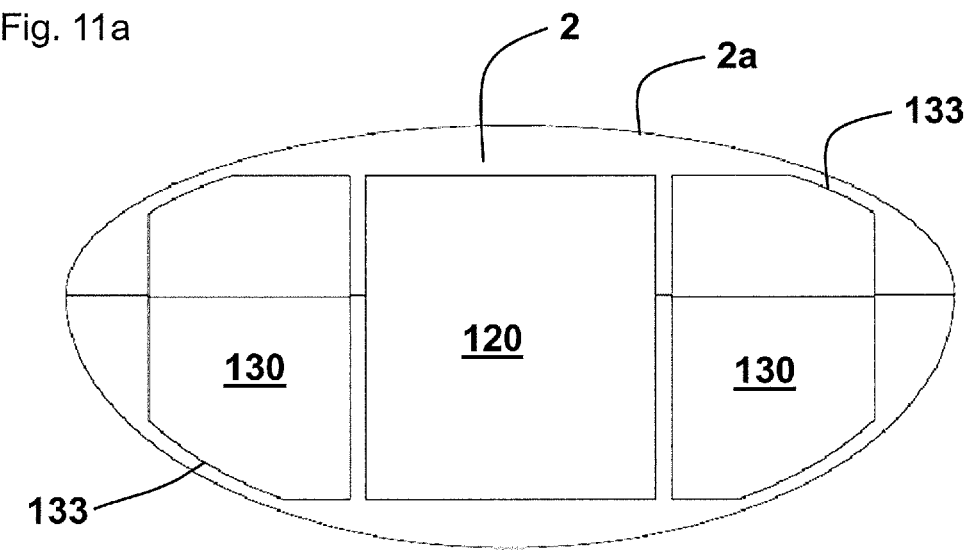
Figure 11B:
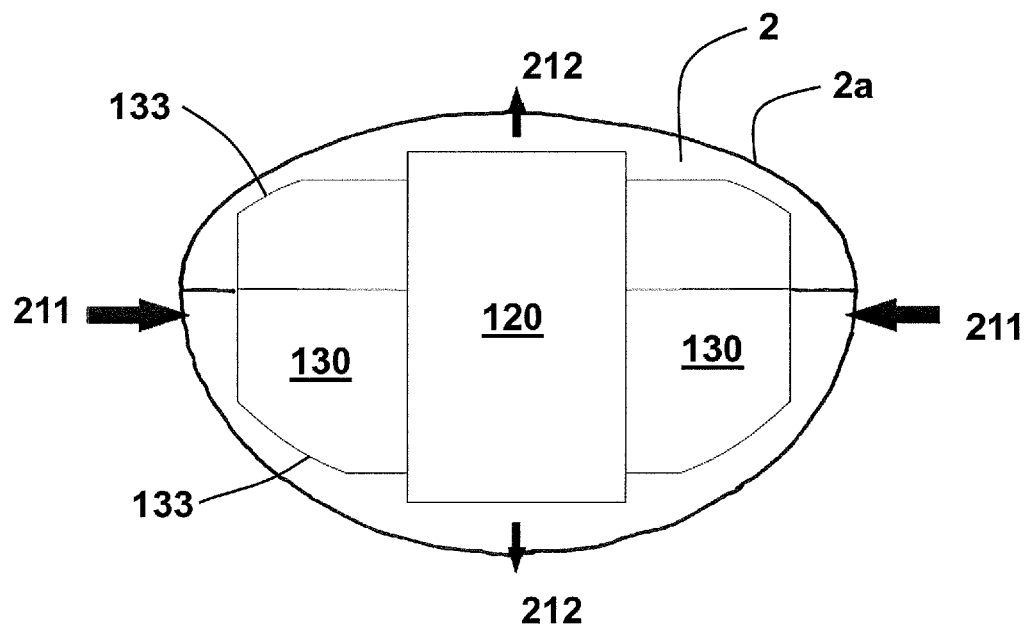

Preferred embodiments of the invention shall now be described with reference to the attached drawings in which:

FIG. 1: is a schematic cross-section through a human eye with the iris in a non-dilated state before treatment of the eye;

FIG. 2: is a schematic cross-section through a human eye with the iris a dilated state during treatment of the eye;

FIG. 3: is a schematic cross-section for a human eye with the iris in a non-dilated state after treatment of the eye; and FIGS. 4*a*-4*d*: are examples of possible locations of lesions which act as compression zones within the crystalline lens;

FIGS. 5*a*-5*d*: are three-dimensional views of further examples of possible locations of lesions which act as compression zones within the crystalline lens;

FIG. 6: is a schematic cross-section through a crystalline lens in a plane perpendicular to the optical or visual axis of the eye;

FIG. 7: is a schematic cross-section through a crystalline lens in a plane parallel to the optical or visual axis;

FIG. 8: is a schematic cross-section through a crystalline lens in a plane perpendicular to the optical or visual axis of the eye in an accommodated state;

FIG. 9: is a schematic cross-section through a crystalline lens in a plane parallel to the optical or visual axis in an accommodated state;

FIG. 10: is a partial schematic cross-section through a crystalline lens in a plane perpendicular to the optical or visual axis of the eye comparing an accommodated and a non-accommodated state;

FIG. 11: are schematic cross-sections through a crystalline lens in a plane parallel to the optical or visual axis of the eye comparing an accommodated and a non-accommodated state; and FIGS. 11*a*-11*b*: are schematic cross-sections through a crystalline lens in a plane parallel to the optical or visual axis of the eye comparing an accommodated and a non accommodated state; and FIGS. 12*a*-12*d*: are schematic depictions of a compression zone.

Figure 13:
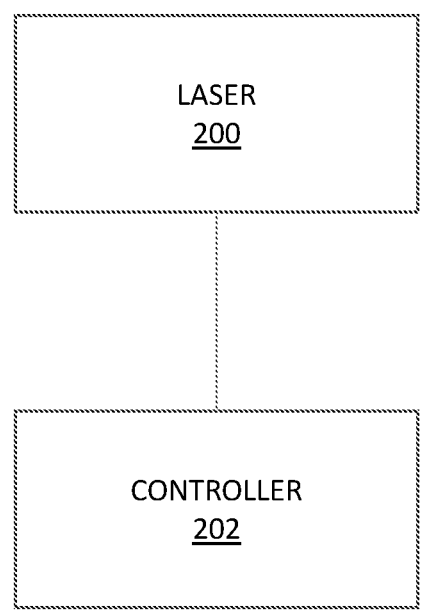

FIG. 13: is a system diagram illustrating a laser 200 operatively coupled to a controller 202.

FIGS. 1-3 show a human eye in cross-section in three different states before (FIG. 1), during (FIG. 2), and after (FIG. 3) a treatment of a crystalline lens. As far as features in the figures have the same or similar functions, they are depicted with the same numerals in the different drawings.

The human eye 1 is depicted in FIGS. 1-3 with a crystalline lens 2, a capsule 2*a* surrounding the crystalline lens, an optical axis 8*a*, a cornea 3, and an iris 4 covering the crystalline lens 2. The iris 4 has an opening, the pupil. In the state before the treatment (FIG. 1) and in the state after the treatment (FIGS. 3, 4), the iris 4 is in a non-dilated state with an opening 4*a* having a smaller diameter than during the treatment (FIG. 2) where the iris 4 is in a dilated state with an opening 4*b* having a larger diameter than in the non-dilated state.

During the treatment, as depicted in FIG. 2, a laser 5 is used to produce a plurality of lesions 6 forming compression zones within the crystalline lens 2. The laser 5 has a focal point 5*b* and a radiation conus 5*a* depending on an aperture of the laser 5.

Preferably, at least one reference point 8 (depicted in FIG. 1) of the crystalline lens 2 is identified and a starting point and an end point of each lesion relative to the reference point 8 are defined prior to producing the lesions 6. The plurality of lesions 6 are located within the crystalline lens 2 and spaced apart from the capsule 2*a* of the crystalline lens 2, preferably about 100-500 micrometer from the capsule 2*a* of the crystalline lens 2 in a direction towards the center of the crystalline lens 2. The capsule 2*a* and the volume adjacent to or beneath the capsule 2*a* thus remain intact and without lesions. Further, the starting point and the end point of each cut are defined such that the lesions 6 and the compression zones do not overlap but multiple single lesions spaced apart from each other are produced rather than lesions that overlap and thus form one continuous lesion. Thus, it is ensured that the multiple lesions only change the characteristics of the lens with respect to flexibility but do not lead to a significant change in volume of the lens.

After the plurality of lesions 6 has been produced by laser pulses or multiple laser pulses emitted by the laser 5, the state after the treatment depicted in FIG. 3 is reached. As can be seen from FIG. 3, the lesions 6 are produced inside the crystalline lens 2 within an annular region 7 of the crystalline lens 2. The annular region 7 extends in a first plane 7a between an inner diameter 7c and an outer diameter 7d. Further, the annular region 7 has an extension 7e in a direction of the optical axis of the eye that is approximately perpendicular to the first and the second planes 7a, 7b or the visual axis respectively. This axial extension of the annular region 7 is least a few millimeter, preferably 1-3 millimeter, and dimensioned such that the annular region 7 is fully located within the crystalline lens 2. In the embodiments depicted in FIG. 3, the annular region 7 has the shape of a section of a hollow cylinder, wherein the inner and outer diameter of the annular region 7 in a second plane 7b correspond to the inner diameter 7b and the outer diameter 7d in the first plane 7a.

As can be seen from FIGS. 2 and 3, the outer diameter 7d of the annular region 7 is smaller than the diameter of the opening 4b of the iris 4 in the dilated state. Further, the inner diameter 7c of the annular region 7 is larger than the diameter of the opening 4a of the iris 4 in the non-dilated state.

Prior to producing the lesions 6 as depicted in FIG. 2, the iris 4 is dilated by dilating drugs applied to the patient. The iris 4 is preferably dilated such that the diameter of the opening 4b of the iris (pupil) in the dilated state is larger than the outer diameter 7d of the annular region 7. Further, the central point of the opening 4a, 4b of the iris 4 and a center of the annular region 7, are both located on a single axis perpendicular to the first plane 7a.

Preferably, prior to dilating the iris 4, the diameter of the opening 4b of the iris 4 in the non-dilated state is measured and the inner diameter 7c of the annular region 7 is defined such that it is equal to or larger than the diameter 4b of the iris 4 in the non-dilated state. It is particularly preferred to measure the diameter of the opening 4b of the iris 4 in the non-dilated state in a dim environment or in darkness in order to identify a maximal diameter 4b of the iris 4 in the non-dilated state of an individual patient.

Further, it is preferred, that during the treatment as depicted in FIG. 2, prior to producing the lesions 6 and after dilating the iris 4, the diameter of the opening 4b of the iris 4 in the dilated state is measured and the outer diameter 7d of the annular region 7 is defined such that it is smaller than the diameter 4b of the iris 4 in the dilated state. It is further preferred, that the outer diameter 7d of the annular region 7 is also prior to producing the lesions 6 defined depending on the distance in a direction of the optical axis of the eye or the visual axis respectively between the opening 4b of the iris 4 and the respective lesions 6 that are to be produced and located between the first plane 7a and the second plane 7b. It is further preferred, that the outer diameter 7d of the annular region 7 is also defined depending on the characteristics of the laser 5, particularly the diameter of the focal spot size of the emitted laser pulse and the location of the focal point were the distance between the aperture and the focal point respectively as well as the intensity of the emitted laser pulses, a wavelength of the emitted pulses, a pulse duration of the emitted pulses, or a repetition rate of the emitted pulses. Preferred laser specifications are the following: numerical aperture of approx. 0.01-0.6, preferably 0.15-0.35, wave length of 800-1400 nm, pulse length of 1 fs-1000 fs, pulse energy of 1 pJ-1 mJ.

FIGS. 4a-d show examples of possible locations 10a-d of lesions forming compression zones within the crystalline lens 2 and behind the iris 4.

Figure 5A:
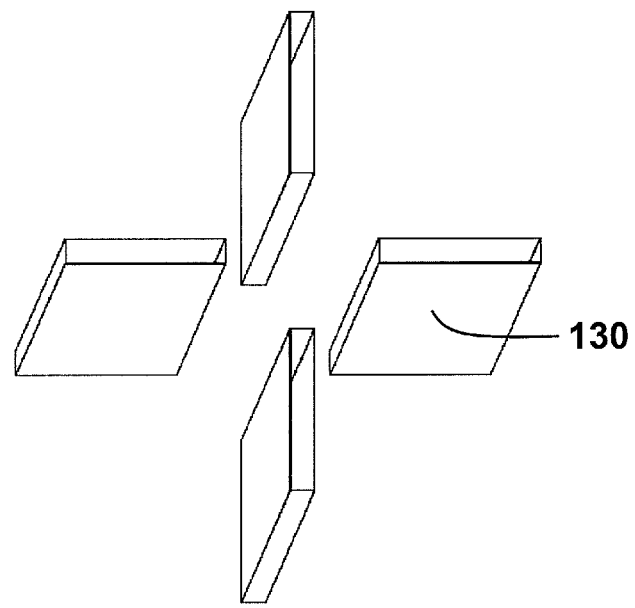
Figure 5B:
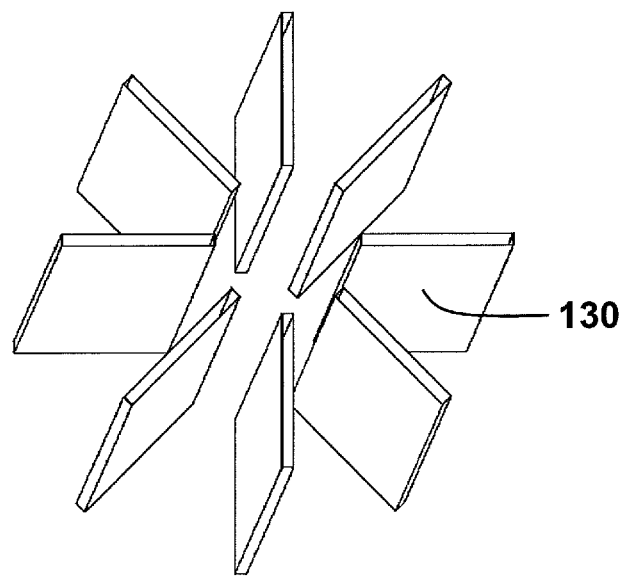
Figure 5C:
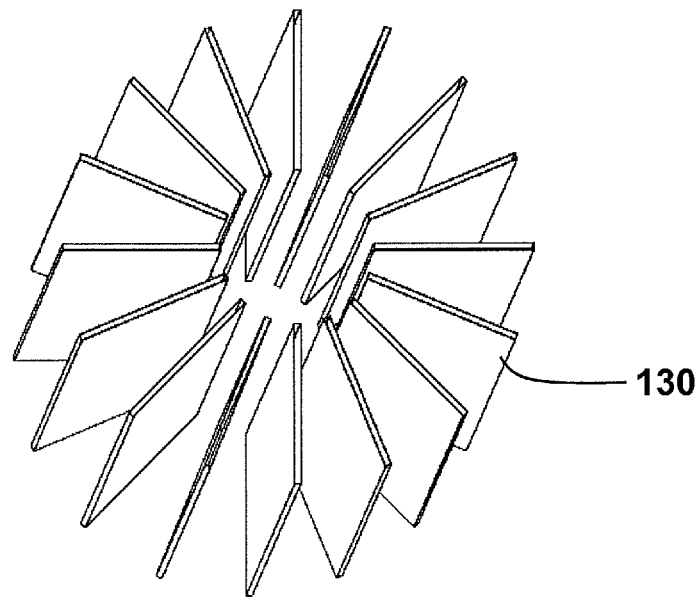
Figure 5D:
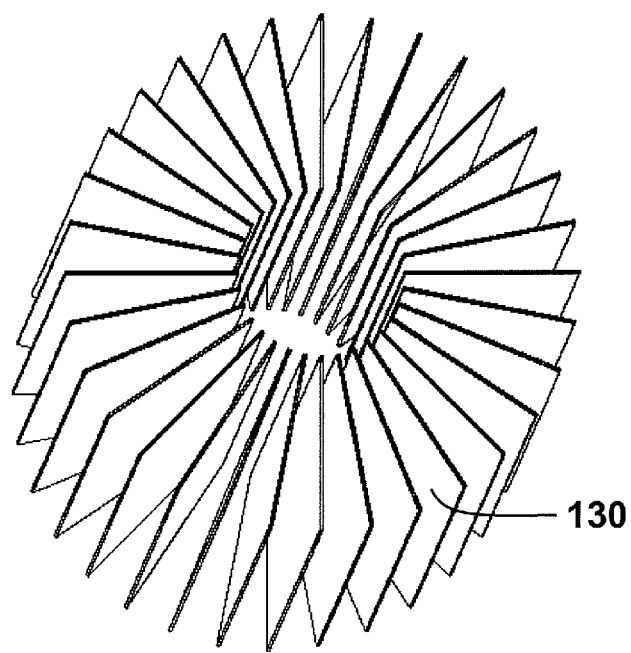

FIGS. 5a-d show three-dimensional views of examples of possible locations of compression zones within the crystalline lens 2 and behind the iris 4, with 4 compression zones 130 forming a cross-like pattern in FIG. 5a, 8 compression zones 130 forming a star-like pattern in FIG. 5b, 16 compression zones 130 forming a star-like pattern in FIGS. 5c, and 32 compression zones 130 forming a star-like pattern in FIG. 5c.

FIGS. 6-10 show cross-sections through a crystalline lens 2 with a lens nucleus 120 and a lens cortex 110 in a plane perpendicular to the optical or visual axis of the eye (FIGS. 6, 8, 10) and in a plane parallel to the optical or visual axis (FIG. 7, 9). FIGS. 6, 7 show the lens in a non-accommodated state; FIG. 8, 9 in an in an accommodated state. In FIG. 10, both states are compared.

The lens nucleus has a diameter 122, The lens nucleus 120 further has an extension 101 in a direction parallel to the optical or visual axis in a non-accommodated state. The lens cortex 110 has an extension 112 in a radial direction in relation to a center of the lens and in a plane perpendicular to the optical or visual axis in a non-accommodated state. The lens cortex 110 further has an extension 101 in a direction parallel to the optical or visual axis.

Each of the 8 compression zones 130 has a length 112 in a radial direction in relation to a center of the lens and in a plane perpendicular to the optical or visual axis corresponding to an extension 112 of the lens cortex 110 in a radial direction in a plane perpendicular to the optical or visual axis. Each of the 8 compression zones 130 further has a depth 101 in a direction parallel to the optical or visual axis corresponding to an extension 101 of the lens cortex 110 in a direction parallel to the optical or visual axis. Each of the 8 compression zones 130 further has an average width 131 in a direction parallel to a tangent of the lens cortex 110 and in a plane perpendicular to the optical or visual axis of the eye. The compression zones 130 depicted in FIG. 6 have the form of a cuboid. Alternatively, compression zones may have the form of a segment of a cylinder, for example. In the cross section depicted in FIG. 6, the cross section of compression zones having the form of a segment of a cylinder would have the form of a segment of a circle.

In FIG. 6, 7, the lens is shown in its non-accommodated state, which means the ciliary body (not shown) is dragging in radial direction 201 and flattens the lens nucleus 120 in the direction 202. As can be seen from FIGS. 6, 7, the compression zones 130 are arranged equidistant to each other in a direction circumferential of the lens cortex 110 or the lens nucleus 120.

The compression zones 130 of width 131 enable the lens cortex 110 to move towards the lens nucleus 120 in the direction 211 when the drag force of the ciliary muscle (not shown) releases (accommodation) and the lens capsule 102 pushes the lens cortex 110 inwards in a direction 211 due to its applied surface tension. Hence the radius of the lens nucleus 120 will be compressed by a distance 111 and the lens nucleus 120 will be elongated in its vertical direction 212 by a distance 123. As a result, the complete lens becomes thicker in its vertical direction 212 and smaller in its radial direction 211. Typically an increase in lens thickness of about 80 micrometer (and a subsequent decrease in its diameter) results in a gain of 1 diopter of gain in accommodation amplitude due to the decrease in the radius of curvature of the lens (not shown). Typically the nucleus 120 of a crystalline lens has length 101 of 40 mm and a radius of 15 mm. During accommodation (compression of the nucleus 120) the volume of the nucleus 120 keeps constant.

If the lens cortex 110 is divided into 8 segments by creating 8 three-dimensional compression zones, each comprising a plurality of lesions, with a width 131, the total circumference of the nucleus 120 reduces by the eightfold of the individual width 131 during accommodation (compression) if all 8 compression zones are reduced to a width of 0. To increase the accommodation ability by 3 diopter which corresponds to a shift of the cortex segments of 45 micrometer the cumulative width calculated by summing up the individual width of all compression zones has to be approximately 280 micrometer. If for example the cortex 110 is divided into eight segments (leading to 8 compression zones 131), the compression zones between each segment have to be compressed by 35 micrometer. Having 56 compression zones, the compression per zone is only 5 micrometer. A compression zone generated by a femtosecond laser will increase the compression ability of that zone by 10%, depending on the density of the applied laser spots per volume. So the laser treatment zone of a compression zone to increase the accommodation ability is approximately 10 times the calculated average width of a compression zone.

FIGS. 11a-b are schematic cross-sections through a crystalline lens 2 with capsule 2a and nucleus 120 in a plane parallel to the optical or visual axis of the eye. Within the lens cortex of lens 2 compression zones 130 are located. The plane of the cross-sections shown in FIGS. 11a-b comprises two compression zones 130. FIG. 11a shows a non-accommodated state and FIG. 11b an accommodated state. As can be seen from FIGS. 11a-b, the compression zones 130 may have a shape differing from a cuboid volume, particularly having rounded corners 133 in order to match the form of the lens 2 and lens capsule 2a. The compression zones shown in FIGS. 11a-b have a larger depth close to the lens nucleus and a smaller depth in a region with a higher radial distance to the lens nucleus.

Figure 12A:
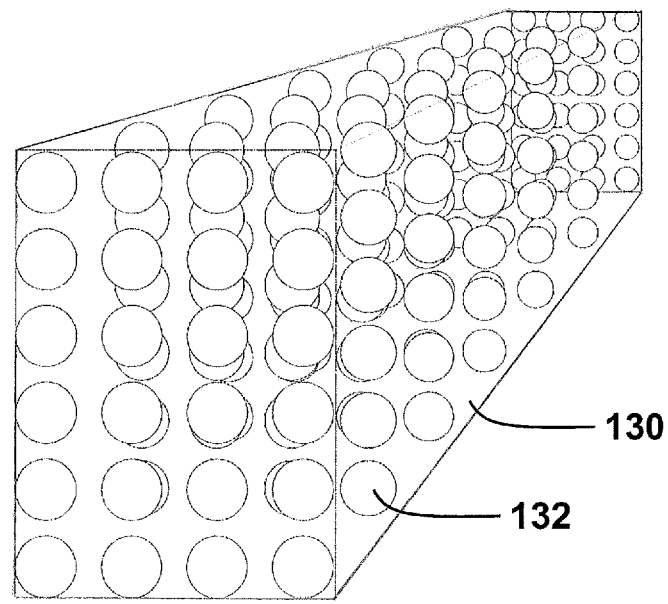
Figure 12B:
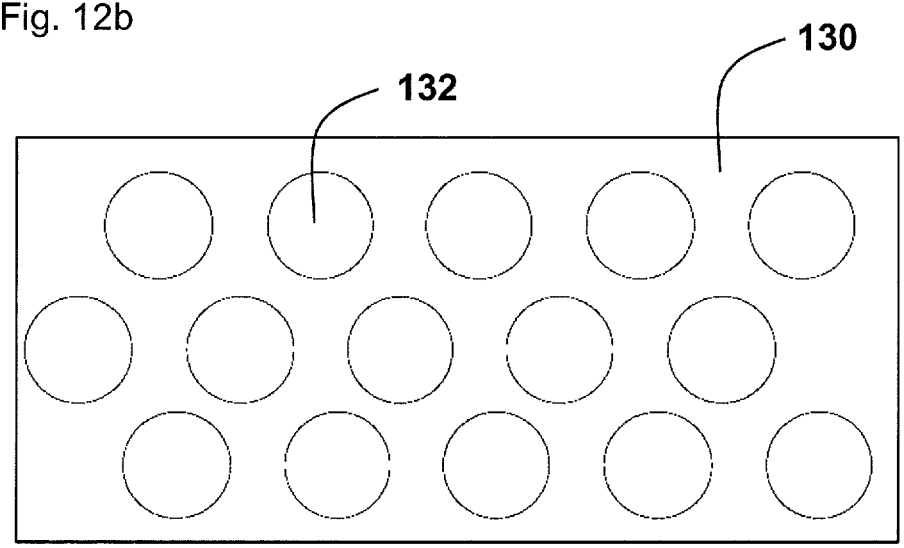
Figure 12C:
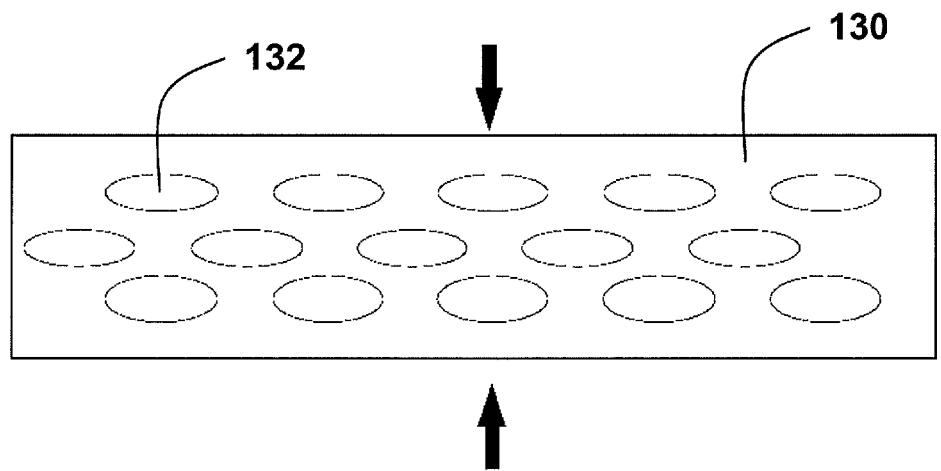
Figure 12D:
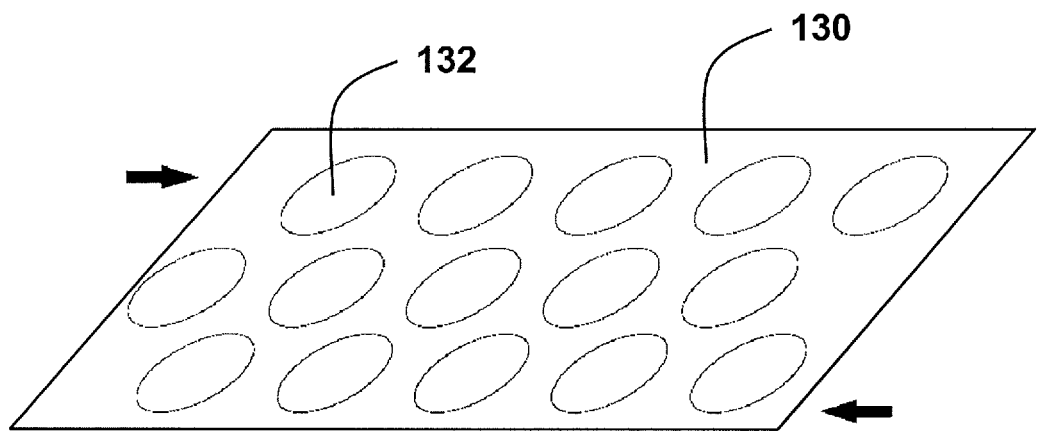

FIGS. 12a-d are schematic depictions of a compression zone 130 comprising a plurality of lesions 132. FIG. 12a depicts the compression zone 130 in a three-dimensional view, FIG. 12b in a cross-section. FIG. 12c depicts a cross-section of the compression zone 130 deformed under compression in the direction of the arrows in FIG. 12c. FIG. 12d depicts a cross-section of the compression zone 130 deformed under shear in the direction of the arrows in FIG. 12d.

The invention claimed is:

1. A laser apparatus comprising:
   a surgical laser; and
   a controller adapted to control the surgical laser, the controller adapted to cause the laser to produce two or more three-dimensional compression zones (130), each comprising a plurality of lesions, inside a lens cortex (110) of a crystalline lens (2) of an eye using a laser pulse or multiple laser pulses, wherein the controller is further adapted such that
   a diameter of a focal spot size or a location of a focal point of the laser is calibrated with respect to a reference point within the crystalline lens, and
   each of the compression zones produced has a length (112) in a radial direction in relation to a center of the lens and in a plane perpendicular to the optical or visual axis corresponding to an extension of the lens cortex in a radial direction in a plane perpendicular to the optical or visual axis, each compression zone extending from an inner circumference of the lens cortex to an outer circumference of the lens cortex,
   each of the compression zones produced has a depth (101) in a direction parallel to the optical or visual axis corresponding to an extension of the lens cortex in a direction parallel to the optical or visual axis, each compression zone having a larger depth close to a nucleus of the lens and a smaller depth further from the nucleus, and
   each of the compression zones produced has an average width (131) in a direction parallel to a tangent of the lens cortex and in a plane perpendicular to the optical or visual axis of the eye,
   wherein the sum of the average widths of all compression zones is 0.1 to 2 millimeter for every 1 diopter of desired gain in accommodation amplitude of the crystalline lens.

2. The laser apparatus according to claim 1,
wherein the width (131) of each of the compression zones (130) varies along the length of the respective zones and the average width is the average value of the varying width.

3. The laser apparatus according to claim 1,
wherein the controller is configured to direct the laser pulse or multiple laser pulses such that each of the compression zones (130) has the form of a cuboid or a segment of a cylinder.

4. The laser apparatus according to claim 1,
wherein the controller is configured to direct the laser pulse or multiple laser pulses such that the sum of the average widths (131) of all compression zones (130) is 0.7 to 1.5 millimeter, for every 1 diopter of gain in accommodation amplitude of the crystalline lens.

5. The laser apparatus according to claim 1,
wherein the controller is configured to direct the laser pulse or multiple laser pulses such that the sum of the average widths (131) of all compression zones (130) is 0.75 to 1.2 millimeter, for every 1 diopter of gain in accommodation amplitude of the crystalline lens.

6. The laser apparatus according to claim 1,
wherein the controller is configured to direct the laser pulse or multiple laser pulses such that the average width g in micrometer of each compression zone (131) corresponds to $$g = 10 \frac{2\pi r}{n}\left(1 - \sqrt{\frac{L}{L+(d*80)}}\right);$$

and
wherein r is the radius of the nucleus of the crystalline lens in micrometers, n is the number of compression zones, L is the length of the nucleus of the crystalline lens in a direction parallel to the optical or visual axis in micrometer, and d is the desired gain in accommodation amplitude in diopter.

7. The laser apparatus according to claim 1,
wherein the controller is configured to direct the laser pulse or multiple laser pulses such that the compression zones (130) are spaced in an equidistant manner in a direction circumferential of the lens cortex (110) or the lens nucleus (120).

8. The laser apparatus according to claim 1,
wherein the controller is configured to direct the laser pulse or multiple laser pulses such that four compression zones (130) are arranged in the form of a cross in a plane perpendicular to the optical or visual axis.

9. The laser apparatus according to claim 1,
wherein the controller is configured to direct the laser pulse or multiple laser pulses such that a plurality of compression zones (130) is produced that forms a star-like pattern in a plane perpendicular to the optical or visual axis.

10. The laser apparatus according to claim 1, wherein the controller is configured to direct the laser pulse or multiple laser pulses such that the compression zones (130) are located within an annular region delimited by an inner and an outer diameter (7c, d) in a first plane (7a) of the crystalline lens with respect to the reference point.

11. The laser apparatus according to claim 1,
wherein the controller is adapted to define a starting point and an end point of each compression zone (130) relative to the reference point prior to producing the compression zones.

12. The laser apparatus according to claim 11,
wherein the controller is adapted to define the starting point and the end point of each compression zone (130) such that the compression zones are located within the crystalline lens and spaced apart from a capsule of the crystalline lens.

13. The laser apparatus of claim 11, wherein the average widths of all compression zones is 0.7 to 1.5 millimeter for every 1 diopter of desired gain in accommodation amplitude.

14. A method for treatment of a crystalline lens of an eye with a lens nucleus (120) and a lens cortex (110), wherein two or more three-dimensional compression zones (130), each comprising a plurality of lesions, are produced inside the lens cortex (110) using a laser pulse or multiple laser pulses, wherein the method comprises:

calibrating a diameter of a focal spot size or a location of a focal point of a laser with respect to at least one reference point of the crystalline lens; and applying the laser pulse or multiple laser pulses to the crystalline lens to form the two or more three-dimensional compression zones, wherein each of the compression zones has a length (112) in a radial direction in relation to a center of the lens and in a plane perpendicular to the optical or visual axis corresponding to an extension of the lens cortex in a radial direction in a plane perpendicular to the optical or visual axis, each compression zone extending from an inner circumference of the lens cortex to an outer circumference of the lens cortex, and wherein each of the compression zones has a depth (101) of each compression zone in a direction parallel to the optical or visual axis corresponding to an extension of the lens cortex in a direction parallel to the optical or visual axis, each compression zone having a larger depth close to a nucleus of the lens and a smaller depth further from the nucleus, and each of the compression zones has an average width (131) in a direction parallel to a tangent of the lens cortex and in a plane perpendicular to the optical or visual axis, and wherein the sum of the average widths of all compression zones is 0.1 to 2 millimeter for every 1 diopter of desired gain in accommodation amplitude of the crystalline lens.

15. The method of claim 14, wherein the average widths of all compression zones is 0.7 to 1.5 millimeter for every 1 diopter of desired gain in accommodation amplitude.

* * * * *